US012569589B2

(12) United States Patent
Mok

(10) Patent No.: US 12,569,589 B2
(45) Date of Patent: Mar. 10, 2026

(54) SYSTEM AND METHODS FOR DELIVERING A DERMAL FILLER

(71) Applicant: Allure Medical Spa PLLC, Shelby Township, MI (US)

(72) Inventor: Charles Mok, Shelby Township, MI (US)

(73) Assignee: Allure Medical Spa, P.L.L.C., Shelby Township, MI (US)

( * ) Notice: Subject to any disclaimer, the term of this patent is extended or adjusted under 35 U.S.C. 154(b) by 249 days.

(21) Appl. No.: 18/142,215

(22) Filed: May 2, 2023

(65) Prior Publication Data

US 2024/0366834 A1 Nov. 7, 2024

(51) Int. Cl.
*A61L 27/20* (2006.01)
*G06N 20/00* (2019.01)

(52) U.S. Cl.
CPC .............. *A61L 27/20* (2013.01); *G06N 20/00* (2019.01); *A61L 2300/236* (2013.01); *A61L 2300/402* (2013.01); *A61L 2400/06* (2013.01); *A61L 2430/34* (2013.01)

(58) Field of Classification Search
CPC .............. A61L 27/20; A61L 2300/236; A61L 2300/402; A61L 2400/06; A61L 2430/34
See application file for complete search history.

(56) References Cited

U.S. PATENT DOCUMENTS

| | | | |
|---|---|---|---|
| 2015/0232623 A1* | 8/2015 | Barg | A61K 8/735 |
| | | | 514/626 |
| 2017/0209654 A1* | 7/2017 | Sebban | A61M 25/0643 |

| | | | |
|---|---|---|---|
| 2017/0232148 A1* | 8/2017 | Nguyen | C08J 3/246 |
| | | | 514/180 |
| 2019/0100605 A1* | 4/2019 | Krause | A61L 27/20 |
| 2020/0000968 A1* | 1/2020 | Pollock | A61K 8/735 |
| 2021/0260244 A1 | 8/2021 | Hoennscheidt | |
| 2021/0308332 A1* | 10/2021 | Olsson | A61L 27/20 |

FOREIGN PATENT DOCUMENTS

| | | |
|---|---|---|
| CN | 111249525 A | 6/2020 |
| KR | 10-2201482 B1 | 1/2021 |

OTHER PUBLICATIONS

Diaz-Rodriguez et al, "Targeting joint inflammation for osteoarthritis management through stimulus-sensitive hyaluronic acid based intra-articular hydrogels", Sep. 2021, Materials Science & Engineering C, vol. 128, p. 1-9 (Year: 2021).*

* cited by examiner

*Primary Examiner* — James D Ponton
*Assistant Examiner* — Hong-Van N Trinh
(74) *Attorney, Agent, or Firm* — CALDWELL LLC

(57) ABSTRACT

A system and a method for delivering a dermal filler are illustrated. The system includes a dermal filler, wherein the dermal filler includes an injectable filler, wherein the injectable filler further includes at least a hyaluronic acid and at least a raw material, and a syringe configured to deliver the dermal filler. The method includes obtaining an injectable filler, wherein the injectable filler further comprises at least a hyaluronic acid, modifying the injectable filler by diluting the injectable filler using a raw material, and delivering the modified injectable filler by injecting the modified injectable filler into a patient using a syringe.

13 Claims, 9 Drawing Sheets

805

810

815

Obtaining an Injectable Filler

Modifying the Injectable Filler by Diluting the Injectable Filler Using a Raw Material Delivering the Modified Injectable Filler by Injecting the Modified Injectable Filler Into a Patient Using a Syringe

800

SYSTEM AND METHODS FOR DELIVERING A DERMAL FILLER

FIELD OF THE INVENTION

The present invention generally relates to the field of aesthetic medicine and dermal filler compositions. In particular, the present invention is directed to a system and methods for delivering a dermal filler.

BACKGROUND

Dermal fillers are injectable soft tissue fillers designed to treat various skin conditions by smoothing out skin folds and wrinkles in a person's face due to aging, restoring fat loss and providing volume in the face, correct acne scars, and the like. Skin aging is a progressive phenomenon that occurs over time, which can be characterized by atrophy, slackening, and fattening that are typically associated with dryness, loss of elasticity, and rough texture. The demand for dermal fillers is continuously growing. However, existing dermal fillers fail to improve the safety of the injection as they may cause skin necrosis, stroke, or blindness when they enter a blood vessel.

SUMMARY OF THE DISCLOSURE

In an aspect, a method for delivering a dermal filler is described. The method includes obtaining an injectable filler, wherein the injectable filler further comprises at least a hyaluronic acid, modifying the injectable filler by diluting the injectable filler using a raw material, and delivering the modified injectable filler by injecting the modified injectable filler into a patient using a syringe.

In another aspect, a system for delivering a dermal filler is described. The system includes a dermal filler, wherein the dermal filler includes an injectable filler, and the injectable filler further includes at least a hyaluronic acid and at least a raw material, and a syringe configured to deliver the dermal filler.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to a system and methods for delivering a dermal filler. In some embodiments, delivering the dermal filler includes a modification of an injectable filler by diluting it with a raw material such as sugar alcohol to reduce the risk of severe and/or permanent complications such as blindness when the dermal filler is accidentally injected into a blood vessel near the eyes, vision abnormalities, allergy, temporary scabs, permanent scarring, and the like.

At a high level, aspects of the present disclosure are also directed to a system for the delivery of a dermal filler. In some embodiments, the dermal filler may further comprise at least a collagen, at least an anesthetic, at least a biosynthetic polymer and/or at least transplant fat of a user in order to achieve a long-lasting and more natural look once the dermal filler is injected into the skin of the user.

Aspects of the present disclosure are directed to adding anesthetic to the injectable filler prior to or after the modification of the injectable filler.

Aspects of the present disclosure are directed to a dermal filler with a concentration of hyaluronic acid between 3 mg/g and 30 mg/g.

Aspects of the present disclosure are also directed to a sugar alcohol that may account for 0.1 to 20% of a total weight of the dermal filler.

Exemplary embodiments illustrating aspects of the present disclosure are described below in the context of several specific examples.

Figure 1:
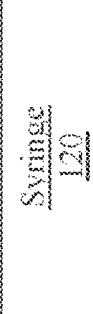
FIG. 1 is a block diagram illustrating an exemplary embodiment of a composition of a dermal filler.
Figure 1:
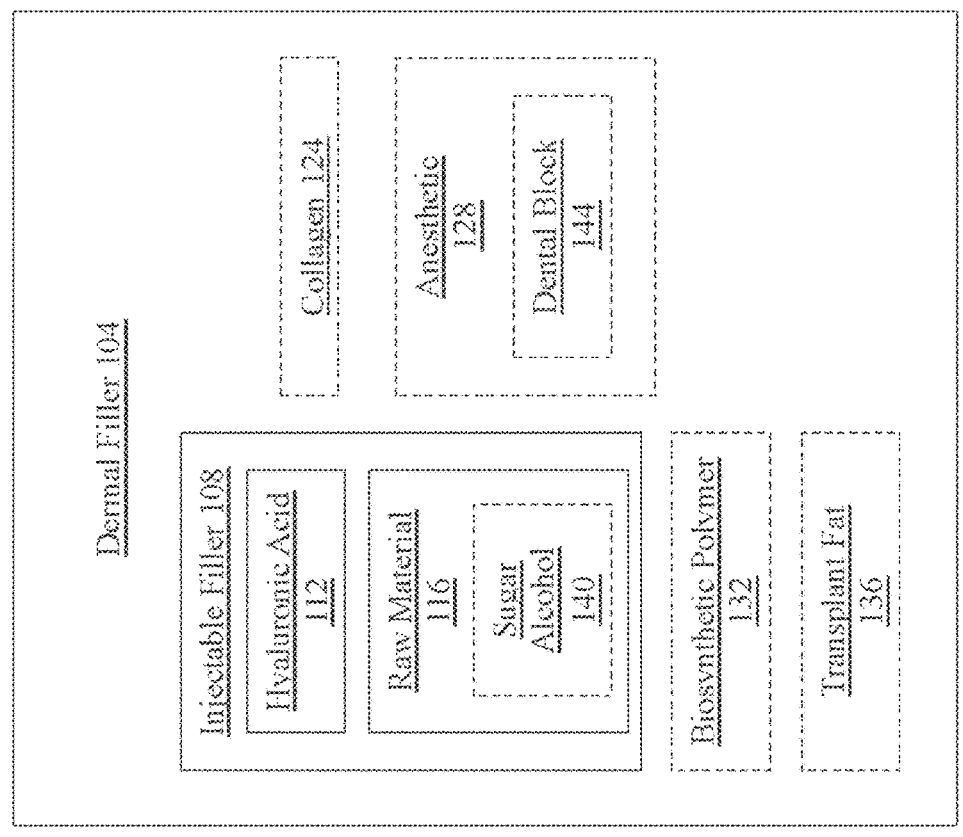
Figure 1:
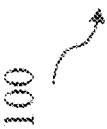

Now referring to FIG. 1, a block diagram illustrating an exemplary embodiment of a system 100 for delivering a dermal filler 104 is presented. As used in this disclosure, a "dermal filler" is a substance that is injected beneath the skin to restore lost volume, smooth lines, soften creases, or enhance facial contours. The term "dermal filler," as used herein, has the same meaning as, and is interchangeably used with the term "soft tissue filler" and should not be construed as imposing any limitations as to the location and type of injection, and it generally encompasses uses at multiple levels beneath the dermis. As used in this disclosure, "soft tissue" is a tissue that connects, supports, or surrounds other structures and/or organs of a human body. In one embodiment, dermal filler 104 includes an injectable filler 108, which may be Juvéderm® injectable gel fillers designed for injections to improve loss of jawlines, correct age-related volume loss, facial wrinkles and folds, augment a specific area such as chins and lips, and the like. In another embodiment, injectable filler 108 may be a gel-like substance made with Hyaluronic Acid (HA), Calcium Hydroxylapatite, Poly-L-lactic Acid, Polymethylmethacrylate, Autologous fat injections, or the like. In a non-limiting example, dermal filler 104 may be used to plump and enhance thin lips, diminish vertical lip lines, enhance shallow contours, soften facial creases and wrinkles, improve the appearance of recessed scars, reconstruct contour deformities in a patient's face, decrease or remove the shadow of the lower lids, and the like. In some embodiments, dermal filler 104 may be configured for injection at a depth of no greater than about 1 mm. In another embodiment, dermal filler 104 may be configured for injection at a depth of no greater than about 0.8 mm. In yet another embodiment, dermal filler 104 may be configured for injections at a depth of no greater than about 0.6 mm. In other embodiments, dermal filler 104 may be configured for injections at a depth of no greater than about 0.4 mm.

Still referring to FIG. 1, in one embodiment, dermal filler 104 includes an injectable filler 108, wherein injectable filler 108 further includes at least a hyaluronic acid 112 and at least a raw material 116, and a syringe 120 configured to deliver dermal filler 104. In some embodiments, dermal filler 104 may further include at least a collagen 124, at least an anesthetic 128, at least a biosynthetic polymer 132, and at least transplant fat 136 of a patient. As disclosed herein, an "injectable filler" is a soft tissue filler injected into the skin of a patient at different depths designed for different medical purposes. A "filler," as used in this disclosure, is a substance injected under the skin of a patient. For instance, the injectable filler may be designed to help fill in facial wrinkles, provide facial volume, augment facial features, and the like. As used in this disclosure, "injectable" means the filler the dermal filler composition is suitable for injection into the skin or other tissue such as lips and face in order to bring dermal filler 104 to a desired target area on a patient. In a non-limiting example, dermal filler 104 is injectable as it can be dispensed from syringe 120 under normal conditions and normal pressure. In some embodiments, injectable filler 108 may be selected from the group of fillers consisting of calcium hydroxylapatite, polycaprolactone, polymethylmethacrylate, and polylactic acid.

Continuing to refer to FIG. 1, a "hyaluronic acid," as used in this disclosure, is a linear polysaccharide consisting of alternating β-1,4-linked units of β-1,3-linked glucuronic acid and N-acetyl-D-glucosamine. The hyaluronic acid is a naturally occurring non-protein glycosaminoglycan (GAG) found in the fluids in the eyes and joints that acts as a cushion and lubricant in the joints and other tissues. As a non-limiting example, Hyaluronic Acid 108, in one embodiment, may be a crosslinked hyaluronic acid using a cross-linking agent such as the industry standard crosslinker 1,4-butanediol diglycidyl ether (BDDE) to prolong the efficacy of HA (>6 months). In another non-limiting example, other chemically modified HAs such as acylated, amidated, esterified and 0-sulfonated HA derivatives, including conjugates of HA with peptides, proteins, vitamins, and fatty acids, may be included. In another non-limiting example, the Hyaluronic Acid may include non-crosslinked components such as a vitamin, for example, vitamin C, a stabilized form of vitamin C, a vitamin C derivative such as l-ascorbic acid 2-glucoside (AA2G), ascobyl 3-aminopropyl phosphate or sodium ascorbyl phosphate (AA2P), and the like. In some embodiments, dermal filler 100 may contain a hyaluronic acid concentration between about 3 mg/g and about 30 mg/g. In other embodiments, dermal filler 100 may contain a hyaluronic acid concentration of about 25 mg/g. In an embodiment, an injectable filler is modified by diluting the hyaluronic acid in a physiological buffer, wherein the physiological buffer comprises 0.9% sodium chloride. In another embodiment, a filler such as Juvéderm® is modified by adding raw material 116 in order to dilute down the Hyaluronic Acid in Juvéderm® to 0.25-0.5 mg. A "raw material," as used in this disclosure is any organic compound that may be added to dilute Hyaluronic Acid. In some embodiments, raw material 116 may be sugar alcohol 140 such as mannitol. In some embodiments, the filler may include a filler with a base of Hyaluronic Acid designed to restore facial contours and improve signs of aging. A "sugar alcohol," as used in this disclosure, is an organic compound derived from sugars, containing one hydroxyl group (—OH) attached to each carbon atom. In some embodiments, sugar alcohol 140 may be selected from the group of sugar alcohols consisting of ethylene glycol (2-carbon), glycerol (3-carbon), erythritol (4-carbon), threitol (4-carbon), arabitol (5-carbon), xylitol (5-carbon), ribitol (5-carbon), mannitol (6-carbon), sorbitol (6-carbon), galactitol (6-carbon), fucitol (6-carbon), iditol (6-carbon), inositol (6-carbon), volemitol (7-carbon), isomalt (12-carbon), maltitol (12-carbon), lactitol (12-carbon), maltotriitol (18-carbon), maltotetraitol (24-carbon), and polyglycitol.

Table 1 illustrates representative dermal filler classifications.

TABLE 1

| Xenogeneic (Bovine/porcine) | Allogeneneic (Human) | Cross-species | Alloplastic | Syngeneic |
|---|---|---|---|---|
| Zyderm I and II | Cosmoderm | Hyaluronic Acids | Radlesse | Fat grafting |
| Zyplast | Cosmoplast Cymetra (micronized alloderm) | Captique Hyaloform | Sculptra Artecoll | Isolagen |
| | Fascian (cadaveric fascia) | Juvederm ® | Silicone droplet | |
| | | Restylane | | |

Continuing to refer to FIG. 1, a "syringe," as used in this disclosure, is a reciprocating pump consisting of a plunger that fits within a cylindrical barrel. For instance, in a non-limiting example, the plunger may be linearly pulled and pushed along the inside of the barrel. In another non-limiting example, syringe 120 may be utilized with a needle. In another non-limiting example, syringe 120 may be utilized with a cannula. A "cannula," as used in this disclosure, is a flexible tubing with a blunt tip that is inserted under a patient's skin. A "collagen," as used in this disclosure, is the main structural protein found in skin and other connective tissues such as cartilage, bones, tendons, ligaments, and the like, which consists of amino acids bound together to form a triple helix of elongated fibril known as a collagen helix. In some embodiments, different types of collagen 124, based on how the molecules are assembled, may be utilized for dermal filler 104. For instance, in a non-limiting example, human-based collagens such as autologen, isolagen, dermalogen, and the like may be utilized. An "autologen," as used in this disclosure, is a type of sterilized and purified natural collagen extracted from a patient's skin. An "isolagen," as used herein, is a type of collagen produced by cloning collagen cells that are obtained from the area behind the patient's ear. A "dermalogen," as used in this disclosure, is collagen made from human skin. In another non-limiting example, bovine collagens may be utilized. A "bovine collagen," as used in this disclosure, is sterilized and purified collagen obtained from cows designed to eliminate wrinkles.

Still referring to FIG. 1, an "anesthetic," as disclosed herein, is an agent that produces a local or general loss of sensation and/or awareness by acting on the brain or peripheral nervous system to suppress responses to sensory stimulation. In some embodiments, anesthetic 128 may be selected from the group of topical anesthetics consisting of benzocaine, lidocaine, proparacaine, oxybuprocaine, butamben, dibucaine, pramoxine, proxymetacaine, tetracaine, triple anesthetic gel of benzocaine, lidocaine, and tetracaine (BLTgel). In some embodiments, anesthetic 128 may further include a nerve block 144. A "nerve block," as used in this disclosure, is an anesthetic agent injected to the infraorbital nerve or mental nerve through the mouth of a patient. In one embodiment, nerve block 144 may be an inferior alveolar nerve block that acts as a dental block, which involves the insertion of a needle near the mandibular foramen in order to deposit a solution of anesthetic 128 near the nerve before it enters the foramen, a region where the inferior alveolar vein and artery are also present.

Still referring to FIG. 1, dermal filler 104 may include at least a biosynthetic polymer 132. As used in this disclosure, a "biosynthetic polymer" is a polymer that combines synthetic components with biopolymers or moieties prepared as mimics of those found in nature. In some embodiments, biosynthetic polymer 132 may include synthetically modified biopolymers, such as functionalized hyaluronic acid derivatives or labeled proteins via cell-instruction. In one embodiment, biosynthetic polymer 132 may be selected from the group of polymers consisting of proteins, peptides and polypeptides, polylysine, collagens, pro-collagens, elastins, and laminins. In another embodiment, biosynthetic polymer 132 may be selected from the group of polymers consisting of synthetic polymers with hydroxyl, amine, and carboxyl functional groups: poly(vinyl alcohol), polyethylene glycol, polyvinyl amine, polyallylamine, deacetylated polyacrylamide, polyacrylic acid, and polymethacrylic acid. In some embodiments, biosynthetic polymer 132 may be selected from the group consisting of dentric or branched polymers, including dentric polyols and dentric polyamines. In another embodiment, biosynthetic polymer 132 may be selected from the group of polymers consisting of solid surface with hydroxyl, amine, and carboxyl functional groups.

With continued reference to FIG. 1, in some embodiments, dermal filler 104 may include transplant fat of a user 136, wherein transplant fat 136 may be taken from another area of the patient's body and purified for fat grafting. A "fat grafting," as disclosed herein, is autologous fat injections or fat transfer designed to smooth wrinkles, restore lip volume, and the like. In some embodiments, the transplant fat 136 is removed from the patient's belly area and injected into the patient's lips as part of dermal filler 104. In some embodiments, transplant fat 136 may be included for facial rejuvenation by adding volume to facial compartments. For instance, in a non-limiting example, transplant fat 136 may be included in dermal filler 104 for the injections near the eyelids. In another non-limiting example, transplant fat 136 may be included in dermal filler 104 for hand rejuvenation in order to treat aging or other appearance-related issues such as prominent-looking veins and tendons, loss of fullness, thinning skin, arthritis, and the like.

Figure 2:
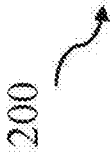
FIG. 2 is a representation illustrating the structure of hyaluronic acid.
Figure 2:
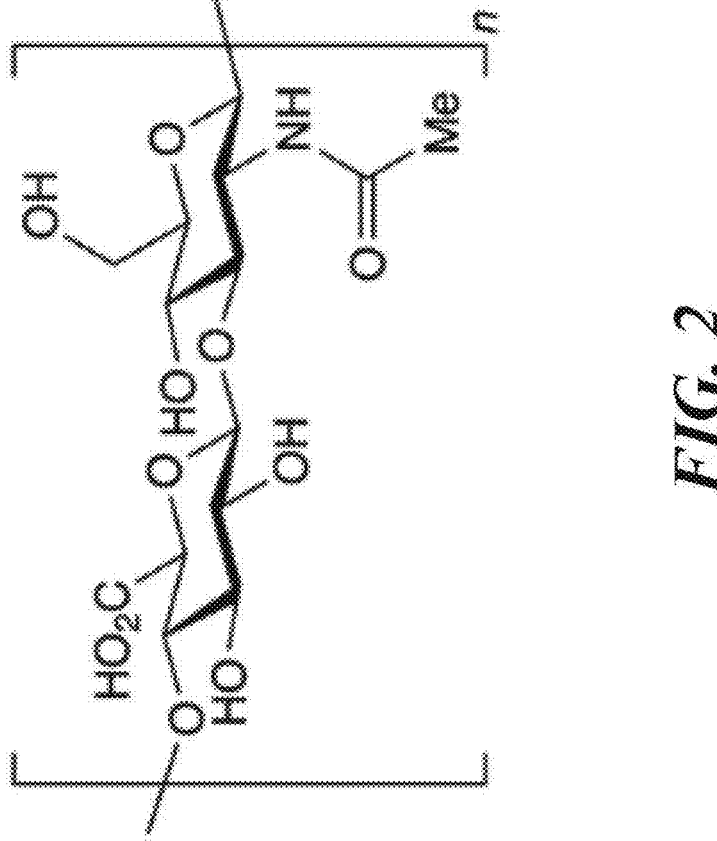

Referring now to FIG. 2, an exemplary representation of the structure of hyaluronic acid 200 is illustrated. Hyaluronic acid 200, also called hyaluronan, is an anionic, nonsulfated glycosaminoglycan distributed widely throughout connective, epithelial, and neural tissues. It is unique among glycosaminoglycans as it is non-sulfated, forms in the plasma membrane. In some embodiments, hyaluronic acid 200 is a polymer of disaccharides, which are composed of D-glucuronic acid and N-acetyl-D-glucosamine, linked via alternating β-1,4-linked and β-1,3-linked glycosidic bonds. In one embodiment, hyaluronic acid may be 25,000 disaccharide repeats in length. In another embodiment, polymers of hyaluronic acid can range in size from 5,000 to 20,000,000 Da in vivo.

Figure 3:
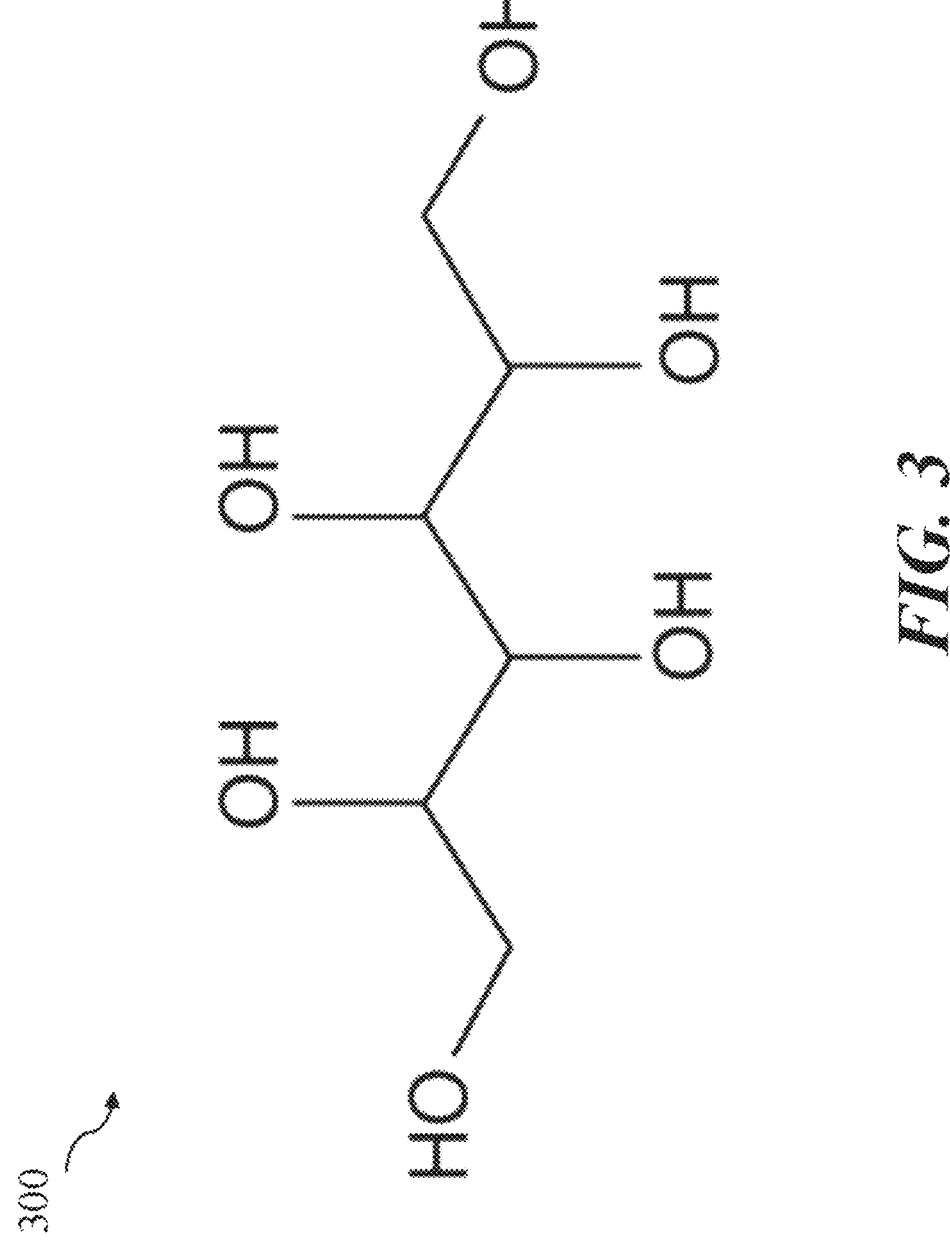
FIG. 3 is a representation illustrating the structure of mannitol.

Referring now to FIG. 3, an exemplary representation of the structure of mannitol as a six-carbon sugar alcohol 300 is illustrated. In one embodiment, dermal filler 100 may be diluted using raw material such as sugar alcohol 300 in order to create a safety barrier and reduce the risk of severe and/or permanent complications such as blindness when dermal filler 100 is injected under a patient's eyes. In some embodiments, sugar alcohol may be selected from the sugar alcohol group consisting of ethylene glycol (2-carbon), glycerol (3-carbon), erythritol (4-carbon), threitol (4-carbon), arabitol (5-carbon), xylitol (5-carbon), ribitol (5-carbon), mannitol (6-carbon), sorbitol (6-carbon), galactitol (6-carbon), fucitol (6-carbon), iditol (6-carbon), inositol (6-carbon), volemitol (7-carbon), isomalt (12-carbon), maltitol (12-carbon), lactitol (12-carbon), maltotriitol (18-carbon), maltotetraitol (24-carbon), and polyglycitol. In some embodiments, in order to make the injectable filler 104 last longer, reduce the risk of post-injection inflammation and preventing degradation of dermal filler 100, and retrieve more natural results, sugar alcohol 300 may account for 0.1 to 20% of the total weight of dermal filler 100 as sugar alcohol has both hydrating and antioxidant properties that make it an ideal excipient. For instance, in a non-limiting example, the presence of sugar alcohol such as mannitol, which is an agent with free radical scavenging properties, may limits the effects of free radicals on the dermis and on dermal filler 100.

Figure 4:
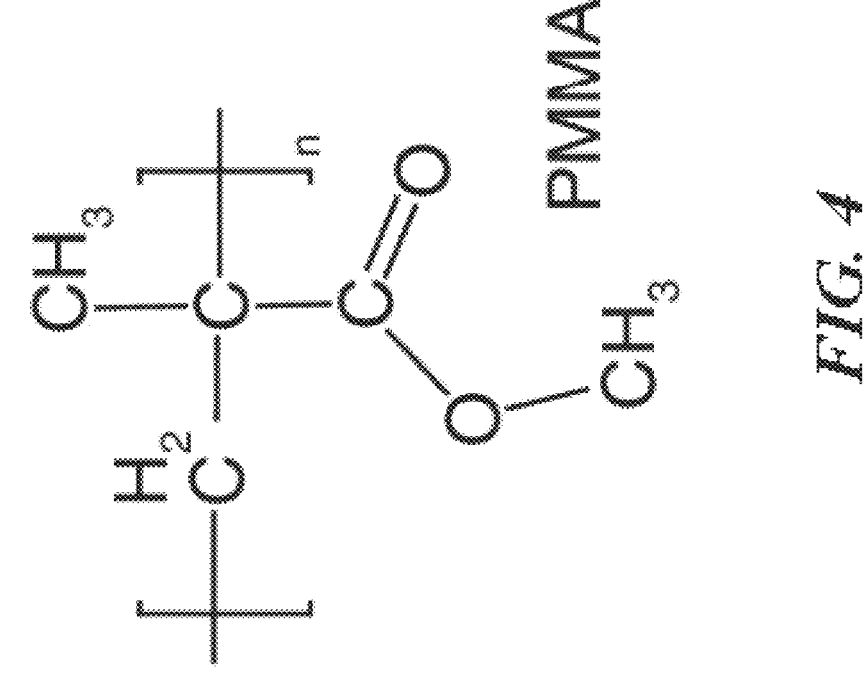
FIG. 4 is a representation illustrating the structure of polymethylmethacrylate.
Figure 4:

Referring now to FIG. 4, an exemplary representation of the structure of polymethylmethacrylate (PMMA) 400 is illustrated. In one embodiment, PMMA 400 is formed by the free radical polymerization of monomer methyl methacrylate. The structure of PMMA 400 is a vinyl polymer which is an ester of methacrylic acid $(CH_2=C[CH_3]CO_2H)$, wherein the pendant $CH_3$ groups hinder the crystalline packing of the polymer chains.

Figure 5:
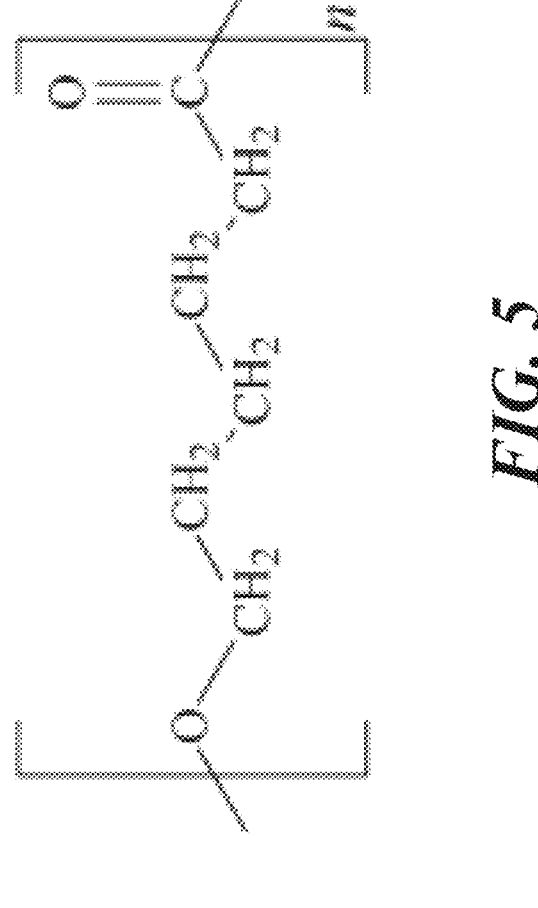
FIG. 5 is a representation illustrating the structure of polycaprolactone (PCL)

Referring now to FIG. 5, an exemplary representation of the structure of polycaprolactone (PCL) 500 is illustrated. In one embodiment, PCL 500 is a biodegradable, semi-crystalline thermoplastic polyester with a low melting point, which is prepared by cationic or anionic ring-opening polymerization of ε-caprolactone using a catalyst such as stannous octoate, dibutyltin dilaurate, and the like. In some embodiments, a wide range of catalysts can be used for the ring opening polymerization of caprolactone. In one embodiment, initiators may be diols such as ethylene glycol or 1,4-butanediol which leads to hydroxyl terminated polymers or oligomers known as "polydiols."

Figure 6:
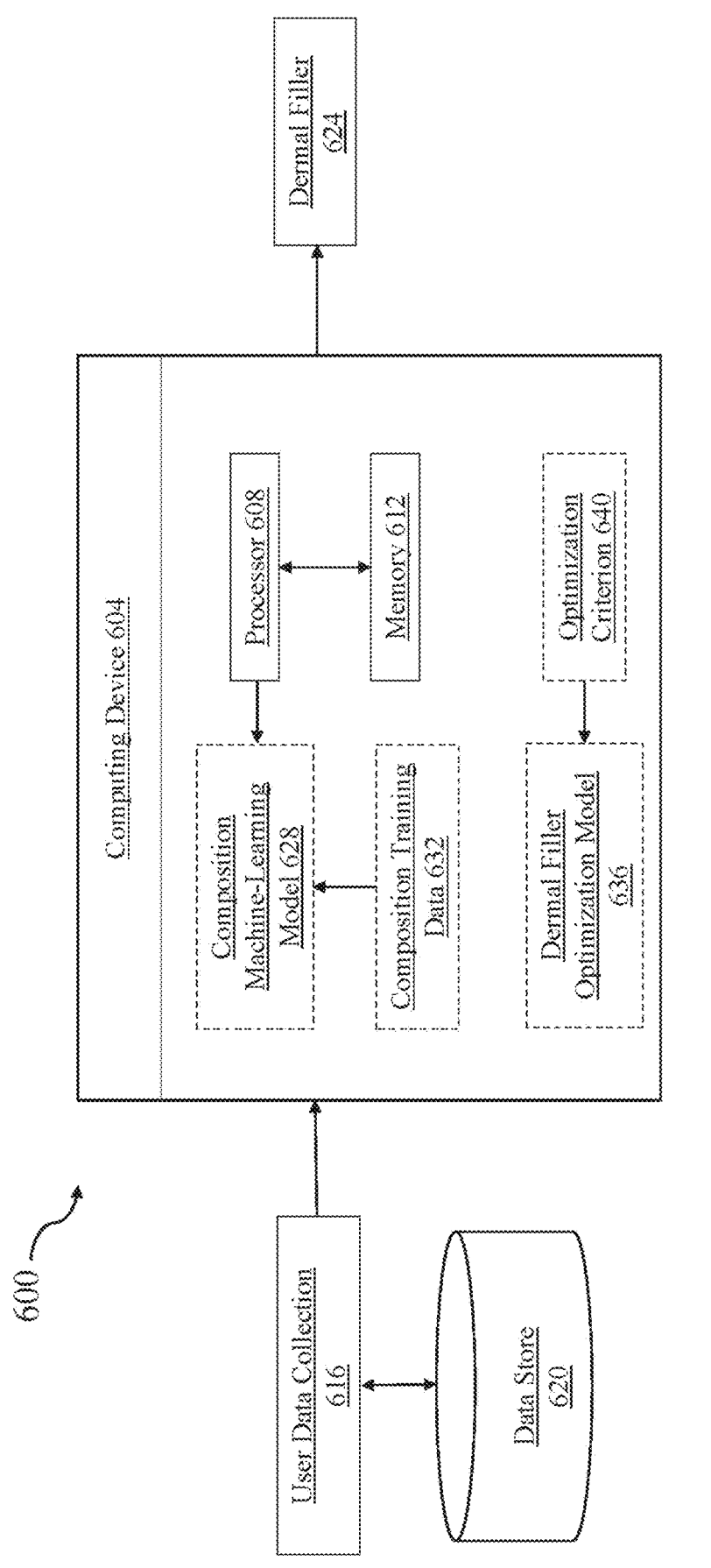
FIG. 6 is an exemplary embodiment of an apparatus for generating the dermal filler composition.

Referring now to FIG. 6, an exemplary embodiment of an apparatus 600 for generating the dermal filler composition is illustrated. In some embodiments, certain aspects of generating the dermal filler composition may be consistent with generating the dermal filler composition as disclosed in U.S. patent application Ser. No. 18/142,198, filed on May 2, 2023, titled "COMPOSITION AND METHODS FOR GENERATING A DERMAL FILLER," which is incorporated by reference herein in its entirety. In one embodiment, apparatus 600 may include a computing device 604, which may include at least a processor 608 and a memory 612 communicatively connected to processor 608, wherein memory 612 contains instructions configuring processor 608 to perform various functions. In one embodiment, and without limitation, processor 608 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 604 may include a single computing device operating independently, or may include two or more computing device operating in concert, in parallel, sequentially or the like; two or more computing devices may be included together in a single computing device or in two or more computing devices. Computing device 604 may interface or communicate with one or more additional devices as described below in further detail via a network interface device. Network interface device may be utilized for connecting computing device 604 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software and the like.) may be communicated to and/or from a computer and/or a computing device. Computing device 604 may include but is not limited to, for example, a computing device or cluster of computing devices in a first location and a second computing device or cluster of computing devices in a second location. Computing device 604 may include one or more computing devices dedicated to data storage, security, distribution of traffic for load balancing, and the like. Computing device 604 may distribute one or more computing tasks as described below across a plurality of computing devices of computing device, which may operate in parallel, in series, redundantly, or in any other manner used for distribution of tasks or memory between computing devices. Computing device 604 may be implemented using a "shared nothing" architecture in which data is cached at the worker, in an embodiment, this may enable scalability of apparatus 600 and/or computing device.

With continued reference to FIG. 6, computing device 604 may be designed and/or configured to perform any method, method step, or sequence of method steps in any embodiment described in this disclosure, in any order and with any degree of repetition. For instance, computing device 604 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 604 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing to refer to FIG. 6, as used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, apparatus and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 6, computing device 604 may be configured to receive user data collection 616. A "user data collection," as used in this disclosure, is any information pertaining to a patient. For instance, user data collection 616 may include, but not limited to, medical records such as prior surgeries including dermal fillers injected at different body parts, the types and/or composition of the dermal fillers injected, known allergies associated with dermal fillers, medications, and the like, health data such as illnesses, age, height, weight, blood type, and the like, demographic data, personal identification, pictures of the patient, and the like. As used in this disclosure, "receive" means to accept, collect, or otherwise gather information from the patient, a device such as a smartphone, a laptop, a desktop, a tablet, and the like, and/or a data store 620 that stores such information. In some cases, user data collection 616 may be a string containing a plurality of words. In some cases, user data collection 616 may be in various format such as, without limitation, txt file, JSON file, word document, pdf file, excel sheet, image, video, audio, and the like thereof. In other cases, user data collection 616 may be present in any data structure described in this disclosure. As used in this disclosure, a "data store" is a collection of information pertaining to patient records. In some embodiments, data store 620 may be a web storage, wherein the web storage is configured for storing user data collection 616. In some embodiments, and without limitation, web storage may include a local storage, wherein the local storage is a web storage that stores user data collection 616 with no expiration date. In other embodiments, and without limitation, web storage may include a session storage, wherein the session storage is a web storage that stores user data collection 616 for a session, wherein the session is a time-delimited two-way link between two or more devices or ends. User data collection 616, in one embodiment, may be stored in a session storage during any processing step described in this disclosure. In another embodiment, data store 620 may include correlating information in user data collection 616 to prior dermal filler injections. For instance, in a non-limiting example, user data collection 616 may include information relating to a patient's prior injections of a dermal filler such as injection volume and filler ingredients, wherein the composition of the dermal filler is customized to avoid the patient's allergies to certain ingredients. In another non-limiting example, user data collection 616 may include information relating to improvements and/or efficacy of a dermal filler composition specifically designed to lift and enhance the natural appearance of the patient's eyes. In yet another non-limiting example, user data collection 616 may include information associated with restoring lost volume near the cheeks and temples, and/or the upper and lower face.

With continued reference to FIG. 6, computing device 604 may be configured to output a composition of dermal filler 624 by analyzing user data collection 616 using a composition machine-learning model 628 trained by composition training data 632. A "composition," is a collection of molecules including relative proportions and/or quantities of elements. Composition may include any composition of a dermal filler designed to treat skin tissue conditions by filling the winkles, providing volume, restoring a smoother appearance, and the like. In one embodiment, the composition of dermal filler 624 may contain a hyaluronic acid concentration between 10 mg/g and 30 mg/g. In another embodiment, the composition of dermal filler 624 may contain a hyaluronic acid concentration between 15 mg/g and 25 mg/g. In yet another embodiment, the composition of dermal filler 624 may contain a hyaluronic acid concentration between 20 mg/g and 25 mg/g. In some embodiments, dermal filler 624 may include at least a hyaluronic acid, at least a collagen, at least sugar alcohol, and/or at least an anesthetic, alone or in combination. In one embodiment, the at least a hyaluronic acid may include a crosslinked hyaluronic acid using a crosslinking agent such as the industry standard crosslinker 1,4-butanediol diglycidyl ether (BDDE) to prolong the efficacy of the dermal filler. In one embodiment, the at least a sugar alcohol may account for 0.1 to 20% of the total weight of the dermal filler. In some embodiments, the at least a sugar alcohol may account for 1 to 20% of the total weight of the dermal filler. In other embodiments, the at least a sugar alcohol may account for 5 to 15% of the total weight of the dermal filler. In other embodiments, dermal filler 624 may include at least the transplant fat of a user and/or at least a biosynthetic polymer, alone or in combination. Composition machine-learning model 628 may be trained with composition training data 632 correlating one or more ingredients of dermal filler compositions with known efficacy and/or known allergy tolerant effects. For instance, in a non-limiting example, composition machine-learning model 628 may be trained to output a composition of dermal filler 624 with high hyaluronic acid concentration of 30 mg/g and high sugar alcohol weight of 20% in order to reduce the likelihood of severe bruising for patients who have a history of severe bruising after the injection. In another non-limiting example, composition machine-learning model 628 may be trained to output a composition of dermal filler 624 with a crosslinked hyaluronic acid using BDDE as a crosslinking agent for patients who have experienced shortened efficacy after receiving an injection of a dermal filler with non-crosslinked hyaluronic acid. A "machine-learning model," as used in this disclosure, is a mathematical and/or algorithmic representation of a relationship between inputs and outputs, as generated using any machine-learning process including without limitation any process as described above and stored in memory; an input is submitted to a composition machine-learning model 628 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 628 may be generated by creating an artificial neural network, such as a convolutional neural network including an input layer of nodes, one or more intermediate layers, and an output layer of nodes. Connections between nodes may be created via the process of "training" the network, in which elements from composition training data 632 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. In some embodiments, composition machine-learning model 628 may include at least a supervised machine-learning process. A "supervised machine-learning process," as defined herein, include algorithms that receive a training set relating several inputs to outputs, and seek to find one or more mathematical relations relating inputs to outputs, where each of the one or more mathematical relations is optimal according to some criterion specified to the algorithm using some scoring function. For instance, a supervised learning algorithm may include inputs and outputs described through this disclosure, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in composition training data 632. Persons skilled in the art, upon reviewing the entirety of this disclosure, will be aware of various possible variations of at least a supervised machine-learning process that may be used to determine relation between inputs and outputs. Supervised machine-learning processes may include classification algorithms as defined above.

Further referring to FIG. 6, machine learning processes may include at least an unsupervised machine-learning processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 6, a "composition training data," as used in this disclosure, is training data stored in a data store that correlates user data collection with dermal filler composition. For instance, as a non-limiting example, composition training data 632 may include information correlating a patient's prior injection history of dermal fillers to the dermal filler composition, wherein the composition of the dermal filler is designed to prevent any allergic reactions based on the patient's health records. In another non-limiting example, composition training data 632 may include information correlating prolonged improvements to a specific dermal filler composition. In another non-limiting example, composition training data 632 may correlate user data from user data collection 616 with a specific range of sugar alcohol needed to modify an injection filler of dermal filler 624. In yet another non-limiting example, composition training data 632 may include manually assigned pairs of specific information from user data collection 616 and dermal filler compositions. Training data may be received from user input, remote computing devices, and/or previous iterations of processing. Computing device 604 is configured to use composition machine-learning model 628, in one embodiment, to input user data collection and output dermal filler composition.

Still referring to FIG. 6, computing device 604 may be configured to generate a dermal filler optimization model 636. In one embodiment, dermal filler optimization model 636 may include an optimization criterion 640. An "optimization criterion," as used in this disclosure, is a value that is sought to be maximized or minimized in a process. For instance, in a non-limiting example, optimization criterion 640 may include any description of a desired value or range of values for one or more attributes of an optimized composition and/or dilution of dermal filler 624; desired value or range of values may include a maximal or minimal value, a range between maximal or minimal values, or an instruction to maximize or minimize an attribute. In a non-limiting example, optimization criterion 640 may specify a range of total quantity of hyaluronic acid utilized for dermal filler 624. In another non-limiting example, optimization criterion 640 may specify a range of sugar alcohol needed for diluting dermal filler 624 in order to reduce a particle size of the injectable filler of dermal filler 624. In another non-limiting example, optimization criterion 640 may specify one or more tolerances for each range. In yet another non-limiting example, optimization criterion 640 may assign weights to different ingredient or values associated with the ingredients; weights, as used herein, may be multipliers or other scalar numbers reflecting a relative importance of a particular ingredient or value. In some embodiments, dermal filler optimization model 636 may be formulated as a linear objective function. Dermal filler optimization model 636 may solve an objective function using a linear program such as without limitation a mixed-integer program. A "linear program," as used in this disclosure, is a program that optimizes a linear objective function, given at least a constraint. For instance, and without limitation, objective function may seek to maximize a total score $\Sigma_{r \in R} \Sigma_{s \in S} c_{rs} x_{rs}$, where R is a set of all users r, S is a set of all dermal filler compositions S, $c_{rs}$ is a score of a pairing of a given user with a given dermal filler, and $x_{rs}$ is 1 if a dermal filler r is paired with a user s, and 0 otherwise. Continuing the example, constraints may specify that each dermal filler is assigned to only one user, and each user is assigned only one dermal filler. Dermal fillers may include any dermal filler as described above. Sets of dermal fillers may be optimized for a maximum score combination of all generated user selections. In various embodiments, a dermal filler optimization model may determine a combination of different ingredients for a dermal filler that maximizes a total score subject to a constraint that all dermal fillers are paired to exactly one user selection. Not all user selections may receive a dermal filler pairing since each user may only receive one dermal filler. A mathematical solver may be implemented to solve for the set of feasible pairings that maximizes the sum of scores across all pairings; mathematical solver may be implemented on computing device 604 and/or another device in apparatus 600, and/or may be implemented on third-party solver.

With continued reference to FIG. 6, dermal filler optimization model 636 may include minimizing a loss function, where a "loss function" is an expression an output of which an optimization model minimizes to generate an optimal result. As a non-limiting example, dermal filler optimization model 636 may assign variables relating to a set of parameters, which may correspond to score dermal filler as described above, calculate an output of mathematical expression using the variables, and select a pairing that produces an output having the lowest size, according to a given definition of "size," of the set of outputs representing each of plurality of candidate ingredient combinations; size may, for instance, included absolute value, numerical size, or the like. Selection of different loss functions may result in identification of different potential pairings as generating minimal outputs. Objectives represented in an objective function and/or loss function may include minimization of plaque buildup. Objectives may include prolonged efficacy of using a dermal filler composition. Objectives may include minimization of potential allergic reactions using a specific composition. Computing device 604 may use composition machine-learning model 628 to generate optimization criteria and/or objective functions.

Still referring to FIG. 6, computing device 604 may be configured to provide a recommendation of dermal filler 624 to a patient. In some embodiments, computing device 604 may receive user feedback about regarding the recommendation of dermal filler 624 such as prior user experience including bruise, side effects, and the like, and actual outcomes of the injection. Computing device 604 may update a recommendation of dermal filler 624 as a function of user feedback. In some embodiments, computing device 604 may be configured to allow adjustments of percentage of each ingredient as a function of user feedback, such as a range of percentage of sugar alcohol, hyaluronic acid, and/or the anesthetic.

Figure 7:
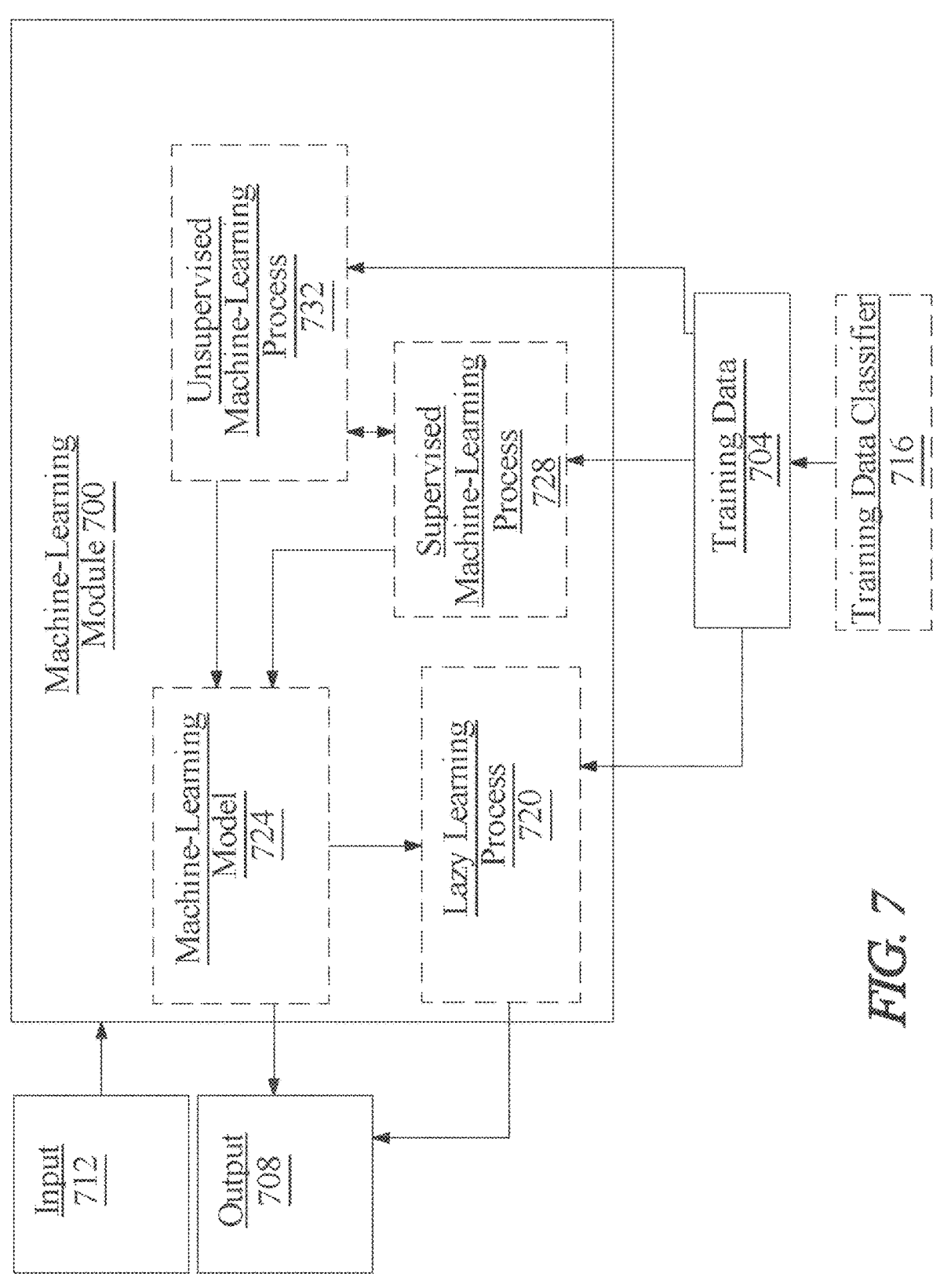
FIG. 7 is a block diagram of an exemplary embodiment of a machine learning module.

Referring now to FIG. 7, an exemplary embodiment of a machine-learning module 700 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 704 to generate an algorithm that will be performed by a computing device/module to produce outputs 708 given data provided as inputs 712; this is in contrast to a non-machine learning software program where the commands to be executed are determined in advance by a user and written in a programming language.

Still referring to FIG. 7, "training data," as used herein, is data containing correlations that a machine-learning process may use to model relationships between two or more categories of data elements. For instance, and without limitation, training data 704 may include a plurality of data entries, each entry representing a set of data elements that were recorded, received, and/or generated together; data elements may be correlated by shared existence in a given data entry, by proximity in a given data entry, or the like. Multiple data entries in training data 704 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 704 according to various correlations; correlations may indicate causative and/or predictive links between categories of data elements, which may be modeled as relationships such as mathematical relationships by machine-learning processes as described in further detail below. Training data 704 may be formatted and/or organized by categories of data elements, for instance by associating data elements with one or more descriptors corresponding to categories of data elements. As a non-limiting example, training data 704 may include data entered in standardized forms by persons or processes, such that entry of a given data element in a given field in a form may be mapped to one or more descriptors of categories. Elements in training data 704 may be linked to descriptors of categories by tags, tokens, or other data elements; for instance, and without limitation, training data 704 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 7, training data 704 may include one or more elements that are not categorized; that is, training data 704 may not be formatted or contain descriptors for some elements of data. Machine-learning algorithms and/or other processes may sort training data 704 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a user's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 704 to be made applicable for two or more distinct machine-learning algorithms as described in further detail below. Training data 704 used by machine-learning module 700 may correlate any input data as described in this disclosure to any output data as described in this disclosure.

Further referring to FIG. 7, training data may be filtered, sorted, and/or selected using one or more supervised and/or unsupervised machine-learning processes and/or models as described in further detail below; such models may include without limitation a training data classifier 716. Training data classifier 716 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 700 may generate a classifier using a classification algorithm, defined as a process whereby a computing device and/or any module and/or component operating thereon derives a classifier from training data 704. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 7, machine-learning module 700 may be configured to perform a lazy-learning process 720 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 704. Heuristic may include selecting some number of highest-ranking associations and/or training data 704 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 7, machine-learning processes as described in this disclosure may be used to generate machine-learning models 724. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 724 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 724 may be generated by creating an artificial neural network, such as a convolutional neural network including an input layer of nodes, one or more intermediate layers, and an output layer of nodes. Connections between nodes may be created via the process of "training" the network, in which elements from a training data 704 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 7, machine-learning algorithms may include at least a supervised machine-learning process 728. At least a supervised machine-learning process 728, as defined herein, include algorithms that receive a training set relating several inputs to outputs, and seek to find one or more mathematical relations relating inputs to outputs, where each of the one or more mathematical relations is optimal according to some criterion specified to the algorithm using some scoring function. For instance, a supervised learning algorithm may include inputs and outputs described through this disclosure, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 704. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 7, machine learning processes may include at least an unsupervised machine-learning processes 732. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 7, machine-learning module 700 may be designed and configured to create a machine-learning model 724 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of one divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 7, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 8:
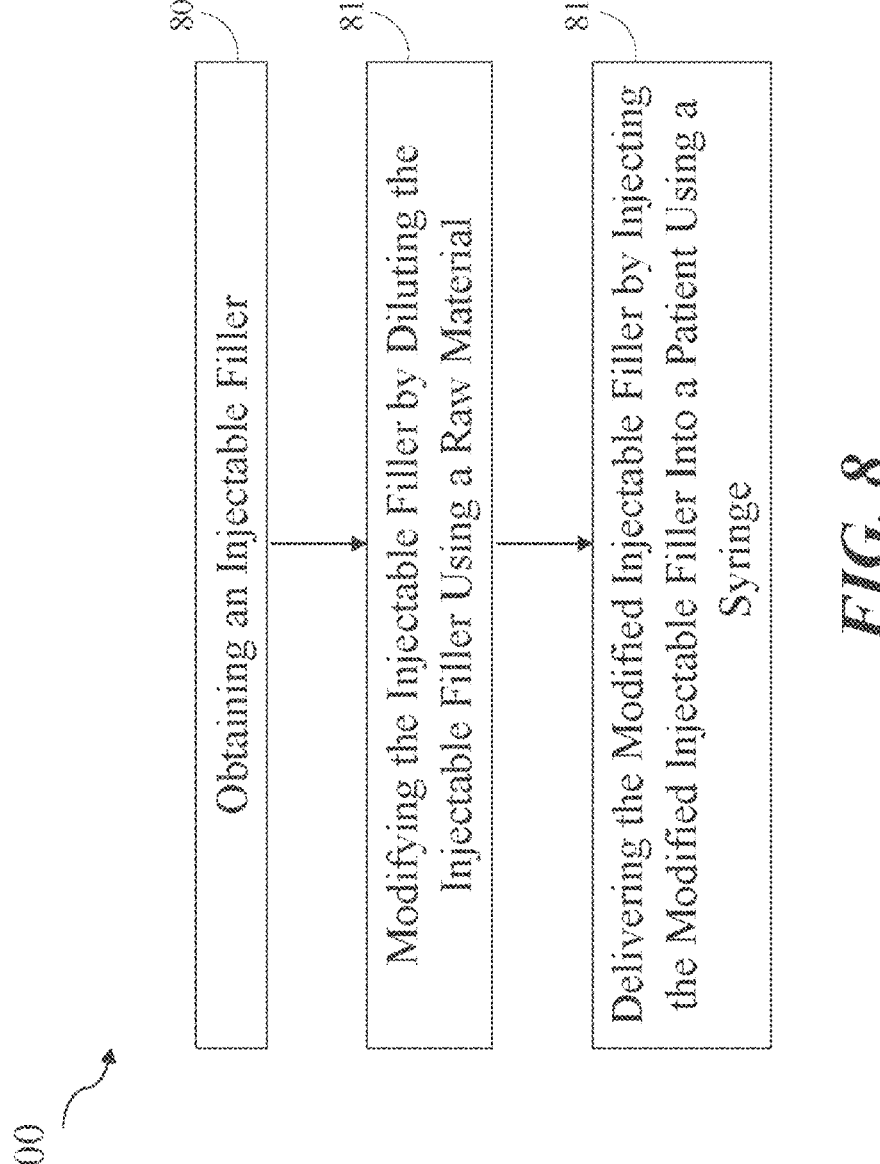
FIG. 8 is a flow diagram illustrating an exemplary embodiment of a method for delivering the dermal filler.

Referring now to FIG. 8, a flow diagram of an exemplary method 800 for delivering a dermal filler is illustrated. At step 805, method 800 includes obtaining an injectable filler, wherein the injectable filler further comprises at least a hyaluronic acid. In one embodiment, the injectable filler may be Juvéderm® injectable gel fillers designed for injections to improve loss of jawlines, correct age-related volume loss, facial wrinkles and folds, augment a specific area such as chins and lips, and the like. In another embodiment, the injectable filler may include at least a Hyaluronic Acid. As a non-limiting example, the Hyaluronic Acid may be a crosslinked hyaluronic acid using a crosslinking agent such as the industry standard crosslinker 1,4-butanediol diglycidyl ether (BDDE) to prolong the efficacy of HA (>6 months). In another non-limiting example, other chemically modified HAs such as acylated, amidated, esterified and 0-sulfonated HA derivatives, including conjugates of HA with peptides, proteins, vitamins, and fatty acids, may be included. In some embodiments, a total quantity of 3 mg/ml-30 mg/ml of HA may be utilized for the injectable filler. In another non-limiting example, the Hyaluronic Acid may include non-crosslinked components such as a vitamin, for example, vitamin C, a stabilized form of vitamin C, a vitamin C derivative such as 1-ascorbic acid 2-glucoside (AA2G), ascobyl 3-aminopropyl phosphate or sodium ascorbyl phosphate (AA2P), and the like. In another embodiment, the injectable filler may include at least a collagen. In some embodiments, different types of collagens, based on how the molecules are assembled, may be utilized. For instance, in a non-limiting example, human-based collagens such as autologen, isolagen, dermalogen, and the like may be utilized. In some embodiments, the dermal filler may include an anesthetic. As a non-limiting example, the anesthetic may include a nerve block such as a dental block. In one embodiment, the anesthetic is added to the injectable filler prior to dilution. In another embodiment, the anesthetic is added to the injectable filler after the dilution. In some embodiments, the injectable filler may include at least transplant fat of a user. In some embodiments, the injectable filler may also include at least a biosynthetic polymer. In a non-limiting example, the at least a biosynthetic polymer may include synthetically modified biopolymers, such as functionalized hyaluronic acid derivatives or labeled proteins via cell-instruction. In one embodiment, the biosynthetic polymer may be selected from the group of polymers consisting of proteins, peptides and polypeptides, polylysine, collagens, pro-collagens, elastins, and laminins. In another embodiment, the biosynthetic polymer may be selected from the group of polymers consisting of synthetic polymers with hydroxyl, amine, and carboxyl functional groups: poly(vinyl alcohol), polyethylene glycol, polyvinyl amine, polyallylamine, deacetylated polyacrylamide, polyacrylic acid, and polymethacrylic acid. In some embodiments, the biosynthetic polymer may be selected from the group consisting of dentric or branched polymers, including dentric polyols and dentric polyamines. In another embodiment, the biosynthetic polymer may be selected from the group of polymers consisting of solid surface with hydroxyl, amine, and carboxyl functional groups. This may be implemented as described and with reference to FIGS. 1-7.

Continuing to refer to FIG. 8, at step 810, method 800 includes modifying the injectable filler by diluting the injectable filler using a raw material. As a non-limiting example, in one embodiment, the injectable filler may be diluted to a range of 0.25-0.5 mg. In some embodiments, the raw material may include at least a sugar alcohol. The sugar alcohol may be selected from the group consisting of mannitol, sorbitol, xylitol, lactitol, isomalt, maltitol, ethylene glycol, glycerol, erythritol, threitol, arabitol, ribitol, galactitol, gucitol, iditol, inositol, volemitol, isomalt, maltotriitol, maltotertraitol, and polyglycitol. In one embodiment, sugar alcohol may account for 0.1 to 20% of a total weight of the dermal filler. In some embodiments, sugar alcohol may account for 1 to 20% of the total weight of the dermal filler. In other embodiments, sugar alcohol may account for 5 to 15% of the total weight of the dermal filler. This may be implemented as described and with reference to FIGS. 1-7.

Still referring to FIG. 8, at step 815, method 800 includes delivering the modified injectable filler by injecting the modified injectable filler into a patient using a syringe. A "syringe," as used in this disclosure, is a reciprocating pump consisting of a plunger that fits within a cylindrical barrel.

For instance, in a non-limiting example, the plunger may be linearly pulled and pushed along the inside of the barrel. In another non-limiting example, the syringe may be utilized with a needle. In another non-limiting example, the syringe may be utilized with a cannula. A "cannula," as used in this disclosure, is a flexible tubing with a blunt tip that is inserted under a patient's skin. In some embodiments, when the diluted injectable filler is transferred to the syringe, the diluted injectable filler may be resized appropriately in accordance with the size of the syringe such that the injectable filler may pass through the needle of the syringe with an acceptable extrusion force as the injectable filler particles are larger than the inner diameter of the needle. In some embodiments, injecting the modified injectable filler further includes utilizing a total quantity of 3 mg/ml-30 mg/ml of at least hyaluronic acid. The modification of the injectable filler is designed to reduce the risk of the injection in certain areas in a user's face as the injection may cause severe and/or permanent complications. For instance, in a non-limiting example, the injection of the diluted dermal filler under the eyes of a user may create a safety barrier so that an inadvertent injection of the filler material into a blood vessel under the eyes of the user does not lead to vision abnormalities, blindness and/or other irreversible damages such as stroke, temporary scabs, and permanent scarring. The diluted dermal filler may also reduce the risk of complications such as tissue ischemia and loss, pulmonary embolization, and the like. For instance, in a non-limiting example, a patient may go blind when an unmodified injectable filler inadvertently hits a blood vessel when it is injected under the eyes of the patient. To improve the safety of the injection, in one embodiment, the modified injectable filler may include diluted hyaluronic acid that is not strong enough to push into the patient's eyes. In one embodiment, the modified injectable filler is injected into the skin of a patient at a depth of no greater than 1 mm. In another embodiment, the modified injectable filler may be configured for injection at a depth of no greater than about 0.8 mm. In yet another embodiment, the modified injectable filler may be configured for injections at a depth of no greater than about 0.6 mm. In other embodiments, the modified injectable filler may be configured for injections at a depth of no greater than about 0.4 mm. This may be implemented as described and with reference to FIGS. 1-7.

It is to be noted that any one or more of the aspects and embodiments described herein may be conveniently implemented using one or more machines (e.g., one or more computing devices that are utilized as a user computing device for an electronic document, one or more server devices, such as a document server, and the like) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, and the like.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, and the like.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
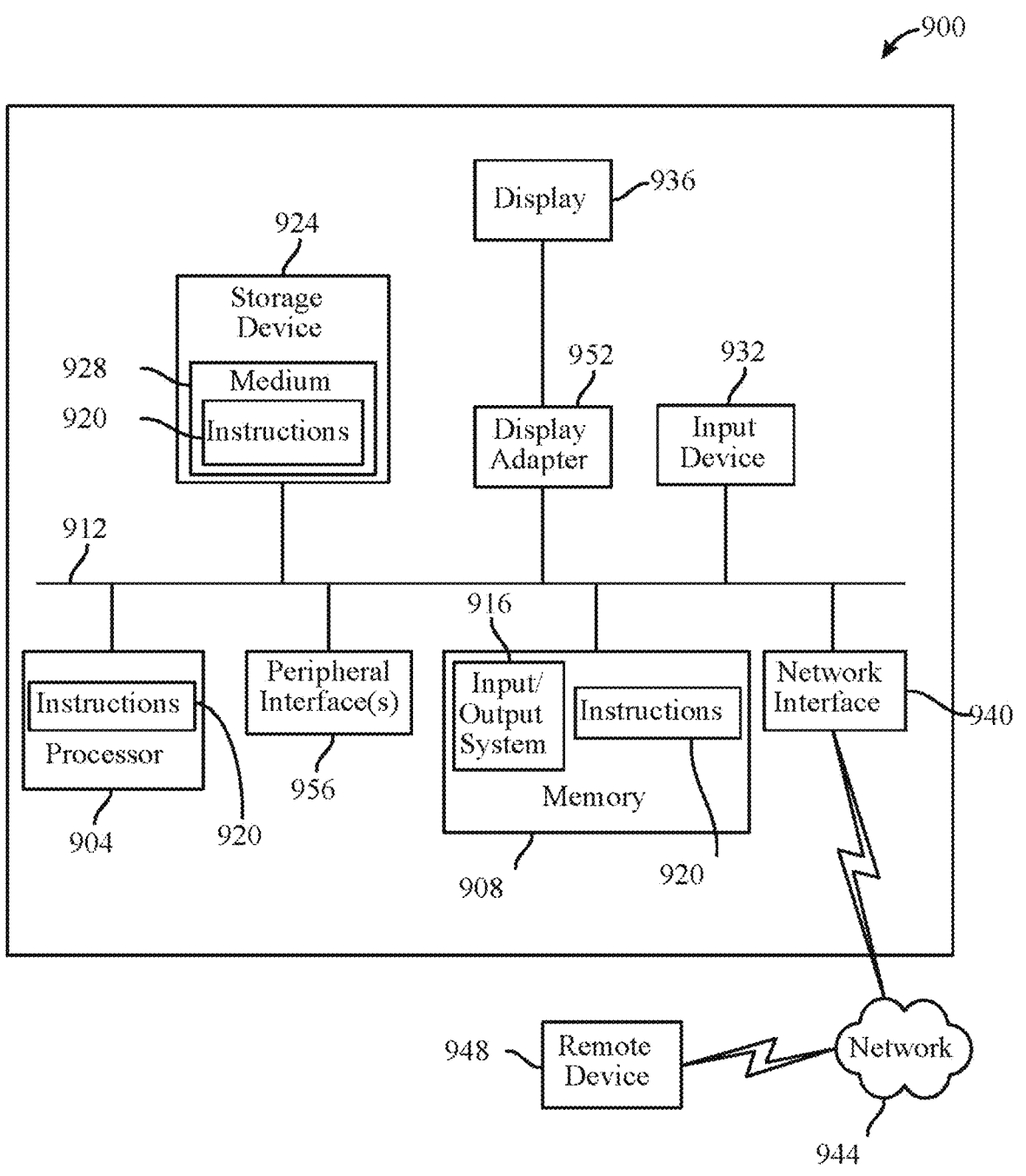
FIG. 9 is a block diagram of a computing system that can be used to implement any one or more of the methodologies disclosed herein and any one or more portions thereof.

Referring now to FIG. 9, FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures. Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, and the like.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, and the like.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, and the like.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above May be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method for delivering a dermal filler, the method comprising:

obtaining an injectable filler comprising transplant fat of a patient, wherein the injectable filler further comprises at least a hyaluronic acid;

modifying the injectable filler, wherein modifying the injectable filler comprises diluting the injectable filler using a raw material; and delivering the modified injectable filler, wherein delivering the modified injectable filler comprises injecting the modified injectable filler under an eye of the patient using a syringe, wherein:

the modified injectable filler is resized in accordance with a size of the syringe such that the modified injectable filler passes through a needle of the syringe with an extrusion force; and diluting the injectable filler comprises diluting the hyaluronic acid to a sufficiently low concentration such that the diluted hyaluronic acid is restrained from adverse pushing against the eye of the patient.

2. The method of claim 1, wherein the raw material comprises at least a sugar alcohol.

3. The method of claim 2, wherein the sugar alcohol accounts for 0.1 to 20% of a total weight of the dermal filler.

4. The method of claim 1, wherein diluting the hyaluronic acid comprises diluting the hyaluronic acid in a physiological buffer.

5. The method of claim 4, wherein the physiological buffer further comprises 0.9% sodium chloride.

6. The method of claim 1, wherein injecting the modified injectable filler further comprises utilizing a total quantity of 3 mg/ml-30 mg/ml of the hyaluronic acid.

7. The method of claim 1, wherein the hyaluronic acid is a crosslinked hyaluronic acid using a crosslinking agent.

8. The method of claim 1, wherein obtaining the injectable filler further comprises outputting a composition of the injectable filler, by a computing device, using user data collection as an input correlating user data from the user data collection with at least a sugar alcohol needed to modify the injectable filler.

9. The method of claim 8, wherein delivering the modified injectable filler further comprises utilizing the computing device to output the composition of the modified injectable filler by analyzing the user data collection using a composition machine-learning model trained by at least a composition training datum.

10. The method of claim 1, wherein the dermal filler further comprises: at least a sugar alcohol.

11. The method of claim 10, wherein modifying the injectable filler further comprises adding at least an anesthetic to the injectable filler prior to the dilution.

12. The method of claim 10, wherein modifying the injectable filler further comprises adding at least an anesthetic to the injectable filler after the dilution.

13. The method of claim 1, wherein the syringe is utilized with a cannula, wherein the cannula comprises a flexible tubing comprising a blunt tip, and wherein the blunt tip is configured to be inserted under a skin of the patient.

* * * * *